United States Patent [19]
Earle et al.

[11] Patent Number: 5,925,518
[45] Date of Patent: Jul. 20, 1999

[54] NUCLEIC ACID PRIMERS FOR AMPLIFICATION OF A MYCOBACTERIA RNA TEMPLATE

[75] Inventors: Steven R. Earle, Durham; Walter E. Jacobson, Raleigh, both of N.C.

[73] Assignee: Akzo Nobel N.V., Arnhem, Netherlands

[21] Appl. No.: 08/448,267

[22] Filed: May 23, 1995

[51] Int. Cl.$^6$ .............................. C12Q 1/68; C12P 19/34; C07H 21/04

[52] U.S. Cl. .................... 435/6; 435/91.2; 536/24.32; 536/24.3

[58] Field of Search ................ 536/24.32, 24.3; 435/91.2, 6

[56] References Cited

U.S. PATENT DOCUMENTS

| | | | |
|---|---|---|---|
| 5,130,238 | 7/1992 | Malek et al. | 435/91 |
| 5,183,737 | 2/1993 | Crawford et al. | 435/6 |

FOREIGN PATENT DOCUMENTS

| | | |
|---|---|---|
| 66727/90 | 5/1991 | Australia . |
| 0318245 | 5/1989 | European Pat. Off. . |
| 0329822 | 8/1989 | European Pat. Off. . |
| 0395292 | 10/1990 | European Pat. Off. . |
| 0398677 | 11/1990 | European Pat. Off. . |
| 0461045 | 12/1991 | European Pat. Off. . |
| 0528306 | 2/1993 | European Pat. Off. . |
| 0639649 | 2/1995 | European Pat. Off. . |
| WO 90/10085 | 9/1990 | WIPO . |
| WO 90/12875 | 11/1990 | WIPO . |
| WO 91/00926 | 1/1991 | WIPO . |
| WO 91/03558 | 3/1991 | WIPO . |
| 9403472 | 2/1994 | WIPO . |

OTHER PUBLICATIONS

Stahl et al. The Division between Fast–and Slow–Growing Species Corresponds to Natural Relationships among the Mycobacteria J. Bacteriology, vol. 172(1), pp. 116–124, 1990.

T. Rogall et al., *International Journal of Systematic Bacteriology*, 40:323–330, Oct. 1990.

W.G. Weisburg et al., *Journal of Bacteriology*, 171:12:6455–6467, Dec. 1989.

Heubner et al., *Journal of Clinical Microbiology*, 31:771–775, 1993.

Earle et al., *American Society for Microbiology*, (Las Vegas), May, 1994.

van der Vliet et al, *Antimicrobial Agents and Chemotherapy*, 38:1959–1965, 1994.

Eisenach et al., *Journal of Infectious Diseases*, 161:977–981, 1990.

Iovannisci et al., *Molecular and Cellular Probes*, 7:35–43, 1993.

Spargo et al., *Molecular and Cellular Probes*, 7:395–404, 1993.

An et al., *Journal of Clinical Microbiology*, 33:860–867, 1995.

Sambrook et al., *Molecular Cloning*, 2nd Edition (1989), pp. 5.34, 5.52–5.55.

Kwoh et al., *Proc. Natl. Acad. Sci.*, 86:1173–1177 (1989).

Fahey et al., *PCR Methods and Applications*, 1:25–34, (1991).

Amann et al., *Applied and Environmental Microbiology*, 58:3007–3011 (1992).

Boddinghause et al., *Journal of Clinical Microbiology*, 28:1751–1759, (1990).

van der Vliet et al., *Journal of General Microbiology*, 139:2423–2429, (1993).

Dunn et al., *Journal of Molecular Biology*, 166:477–535, 1983.

Crestfield et al., *Journal of Biological Chemistry*, 216:185–193, (1955).

*Primary Examiner*—Kenneth R. Horlick
*Assistant Examiner*—Joyce Tung
*Attorney, Agent, or Firm*—Mary E. Gormley

[57] ABSTRACT

Disclosed is a pair of primers to amplify a homologous region of the 16S rRNA of Mycobacteria. The primer pair performs better than a number of other primer pairs in a transcription-based amplification system. The amplified RNA can be detected with known probes for Mycobacteria. The primers, methods and kits are especially useful as an aid in the diagnosis of *M. tuberculosis*.

13 Claims, 4 Drawing Sheets

RNA MARKERS  $10^6$  $10^5$  $10^4$  $10^3$  $10^2$  $10^1$  RNA MARKERS

COPIES OF TEMPLATE

COPIES OF TEMPLATE

FIG. 2B-1

RNA MARKERS  $10^6$ $10^5$ $10^4$ $10^3$ $10^2$ $10^1$  RNA MARKERS

COPIES OF TEMPLATE

COPIES OF TEMPLATE

FIG. 2C-1

RNA MARKERS  $10^6$  $10^5$  $10^4$  $10^3$  $10^2$  $10^1$  RNA MARKERS

COPIES OF TEMPLATE

COPIES OF TEMPLATE

NUCLEIC ACID PRIMERS FOR AMPLIFICATION OF A MYCOBACTERIA RNA TEMPLATE

FIELD OF THE INVENTION

The present invention is directed to the discovery of nucleic acid primers that are useful in the amplification of a Mycobacteria RNA template, particularly *Mycobacteria tuberculosis*. The present invention is also directed to methods of using the primers in an amplification process, as well as a test kit containing the primers and, optionally, one or more probes.

BACKGROUND OF THE INVENTION

Tuberculosis is the most pervasive infectious disease world-wide, causing about 3,000,000 deaths annually. Normally associated with poverty, overcrowding and poor public health systems, the recent surge of tuberculosis cases in the United States correlates with the AIDS epidemic. The rapid progression of the disease in HIV infected persons and the increase in the number of drug resistant tuberculosis strains have highlighted the need for more rapid diagnostic methods.

The current method for rapid diagnosis of tuberculosis used in the clinical laboratory is the screening of acid-fast stained smears by microscopy. However, this method has limited sensitivity and does not differentiate *M. tuberculosis* from other Mycobacteria species. Liquid culture of the organisms coupled with radiometric or colorimetric detection methods offer excellent sensitivity; however, because of the slow rate of growth of Mycobacteria, it requires about 10 days for the detection of *M. tuberculosis*. Definitive species identification requires nucleic acid hybridization or chemical analysis of mycolic acids. (Heubner et al., *Journal of Clinical Microbiology* 31:771–775, 1993.) The disadvantage of direct nucleic acid hybridization assay on patient samples is that it lacks the sensitivity of the aforementioned culture methods. An alternative to amplification of the Mycobacteria by culture is the amplification of mycobacterial nucleic acid, followed by specific identification by nucleic acid hybridization. A number of nucleic acid amplification methods are being developed for mycobacterial testing including NASBA™ (Earle et al., American Society for Microbiology, (Las Vegas), May, 1994; van der Vliet et al., *Journal of General Microbiology* 139:2423–2429 (1993);and van der Vliet et al., *Antimicrobial Agents and Chemotherapy* 38:1959–1965 (1994), polymerase chain reaction (Eisenach et al., *Journal of Infectious Diseases* 161:977–981, 1990), ligase chain reaction (Iovannisci et al., *Molecular and Cellular Probes* 7:35–43, 1993),strand displacement (Spargo et al., *Molecular and Cellular Probes* 7:395–404, 1993) and Qβ replicase (An et al., *Journal of Clinical Microbiology* 33:860–867, 1995). Any of these methods could significantly reduce the time required for diagnosis of infection with *M. tuberculosis*, perhaps to as little as one day.

European patent application, Publication No. 0 528 306 A2 (February, 1993), discloses mycobacterium primers and probes for use in polymerase chain reaction amplification and detection. However, this publication does not show the specificity or efficiency of the disclosed primers in the polymerase chain reaction. In addition, only prophetic examples are given regarding the amplification of mycobacterial 16S rRNA. Moreover, it is accepted in the art that a pair of primers useful in a polymerase chain reaction amplification may not be useful, or as efficient, in a transcription based amplification system such as NASBA™.

An amplification system that has significant advantages over PCR amplification systems is the amplification system referred to as NASBA™ (nucleic acid sequence based amplification). The NASBA™ methodology is disclosed in U.S. Pat. No. 5,409,818 and European application No. 0 329 822, both of which are incorporated herein by reference. The NASBA™ system amplifies RNA, whereas PCR amplifies DNA. As compared to PCR, NASBA™ requires less user participation and fewer manipulations and steps. Another advantage is that NASBA™ is performed at a relatively constant ambient temperature, ensuring that the enzymes used in the process do not lose their activity. Finally, in NASBA™ each cycle of the amplification process generates a plurality of RNA copies from one substrate. Therefore, it is considered preferable to use the NASBA™ system to amplify mycobacterial RNA, which in turn can be detected using nucleic acid probes.

As in any amplification system, one must find suitable primers to amplify the sequence of interest. The need therefore exists for primer sets and hybridization probes that can be used for the amplification and subsequent detection of mycobacterium, particularly *M. tuberculosis/bovis*, which cause human disease. The present invention relates to the discovery of a pair of primers that give a surprisingly high yield of mycobacterial RNA, without any non-specific products, in the NASBA™ system.

SUMMARY OF THE INVENTION

The present invention relates to a pair of primer oligonucleotides that give unexpectedly high yields of product RNA, as compared to other primer pairs. The primer pair of the present invention is derived from the 16S rRNA gene of the mycobacterium tuberculosis complex (*M. tuberculosis/bovis/TB*), which has been extensively studied in the art.

DESCRIPTION OF THE DRAWINGS

FIG. 1: Shows a NASBA™ reaction scheme. In the NASBA™ reaction, single stranded RNA is continuously converted, using reverse transcriptase and RNase H, into a double stranded cDNA template for transcription of additional single stranded RNA by T7 RNA polymerase. Primer 1 contains the polymerase promoter sequence (particularly, the T7 RNA polymerase), indicated by the hook. Dotted lines indicate DNA, solid lines indicate RNA. RT is avian myeloblastosis virus with reverse transcriptase; T7 pol is T7 RNA polymerase; and RNase H is *E. coli* RNase H.

FIGS. 2A–2C show a comparison of efficiency of primer pairs in amplifying *M. bovis* BCG rRNA by gel analysis. The urea-polyacrylamide gels show the RNA products from the NASBA™ reaction by size. The lowest RNA marker is 155 base pairs, the next lowest is 280 base pairs. The size of the expected product is about 250 base pairs. As can be seen in FIG. 2A, with primer pair 201/50.1 the expected product is present at all levels of template, from $10^6$ copies to $10^1$ copy. There is a minor band around 155 base pairs. This is the best primer pair. For primer pair 727A/737A (FIG. 2B) an RNA product of the expected size can be observed only at $10^6$ and $10^5$ copies of template. There is a prominent non-specific product at 155 base pairs, at all levels of template tested. This primer pair is average. Primer pair 202/101 (FIG. 2C) is poor. No product of the expected size is seen from $10^6$ to $10^1$ copies of target. There are always several non-specific products observed around 155 base pairs. The ELGA (enzyme linked gel assay) results show the same trend. There is no product found with 202/101 (the band at the bottom is preprobe, top band is probe hybridized product).

The ELGA result for 727A/737A shows a positive reaction down to $10^5$ copies of template. The ELGA result for 201/50.1 shows a positive result down to $10^4$ copies of template.

DETAILED DESCRIPTION OF THE INVENTION

The present invention is directed to primers that are useful for amplification of M. tuberculosis 16S ribosomal RNA (and the same template from other mycobacterial species) by the NASBA™ system. These primers, which can be completely described by chemical composition and structure, are single stranded DNA. A pair of primers, with each individual primer being unique, is required in the NASBA™ system.

The term "oligonucleotide" as used herein refers to a molecule comprised of two or more deoxyribonucleotides or ribonucleotides such as primers and probes. The term "primer" as used herein refers to an oligonucleotide, whether naturally occurring (for example, as a restriction fragment) or produced synthetically, which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA polymerase or reverse transcriptase. A primer must be sufficiently long to prime the synthesis of extension products in the presence of an agent for polymerase. A typical primer contains at least about 10 nucleotides in length of a sequence substantially complementary to the target sequence, but somewhat longer primers are preferred. Usually primers contain about 15–26 nucleotides, but longer primers, up to 35 nucleotides, may also be employed.

A primer will always contain a sequence substantially complementary to the target sequence, that is the specific sequence to be amplified, to which it may anneal. A primer may, optionally, also comprise a promoter sequence. The term "promoter sequence" defines a single strand (preferably the sense strand) of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage polymerases, such as bacteriophage T3, T7 or SP6.

It is understood that a nucleic acid primer consisting of the sequences of the present invention may contain minor deletions, additions and/or substitutions of nucleic acid bases, to the extent that such alterations do not negatively affect the yield or product obtained to a significant degree.

NASBA™ is an enzymatic process for the amplification of RNA. Two enzymes are required: reverse transcriptase and T7 RNA polymerase. In addition, the reaction may be supplemented with RNase H. The first steps in NASBA™ depend on specific hybridization of DNA primers to initiate cDNA synthesis from the target RNA template by reverse transcriptase. One or both of these primers contain, in addition to specific hybridization sequences, a polymerase promotor sequence, preferably a T7 RNA polymerase promoter sequence. Complete reverse transcription of the RNA template results in a double stranded cDNA containing a T7 (or T3 or SP6) RNA polymerase promotor. Initiation of transcription by T7 RNA polymerase (or T3 or SP6 polymerase) yields multiple copies of the original RNA sequence.

Variations in the NASBA™ method are considered within the scope of the present invention. For instance, one may use "destabilizing" nucleotide triphosphates in the amplification, such as inosine triphosphate disclosed in European patent application No. 92.202564.8, published in 1994. In addition, it is not necessary to use RNase H in the NASBA reaction, because it is known in the art that reverse transcriptase itself has RNase H activity under appropriate conditions, as disclosed in Sambrook et al., *Molecular Cloning,* (1993), incorporated herein by reference. Other variations would be apparent to those skilled in the art.

The oligonucleotides according to the present invention are highly suitable for use as primers in amplification reactions for the amplification, and subsequent detection, of mycobacterial nucleic acid. The oligonucleotides according to the present invention may be linked to a promotor sequence to allow their use as primers in transcription based amplification methods like TAS (Transcription Based Amplification System) (disclosed in Kwoh et al., *Proc. Natl. Acad. Sci.,* 86:1173–1177 (1989), incorporated herein by reference), 3SR (described in Fahey et al., *PCR Methods and Applications,* 1:25–44 (1991), incorporated herein by reference), NASBA™ or even PCR. Normally a set of primers will consist of at least two primers, one "upstream" and one "downstream" primer which together define the target sequence, i.e., the sequence that will be amplified using said primers (the amplificate).

A comparison of 16 pairs of primers for NASBA™ amplification of mycobacterial 16S rRNA was done. Template was either 16S rRNA purified from cultured *M. bovis* BCG, transcript from cloned BCG 16S rRNA gene, or nucleic acid isolated from clinical specimens (NALC/NaOH digested sputa). Amplification results were determined by three methods: (1) denaturing urea polyacrylamide gel; (2) gel assay after hybridization with enzyme labeled probe; and (3) bead based assay in an electrochemiluminescent detector after hybridization with labeled probe. The number of starting molecules of template required for detectable amplification range from $10^1$ to $10^{10}$, depending on the primer pair. Gel analysis showed variation in the length of amplificates depending on primers. The best primer pair gave consistent amplification of 100 copies of template, only one amplification product, and successfully amplified nucleic acid isolated from clinical specimens. Conserved hybridization sequences allow detection of many species of Mycobacteria, with species-specific detection by the use of multiple probes.

The present invention is directed to several pairs of primers, including a preferred pair, for amplification of Mycobacteria 16S ribosomal RNA template using the NASBA™ system. There is a wide variation in the efficacy of primer pairs for NASBA™ amplification of the mycobacterial template. The best primer provides specific amplification of the complete template between the hybridized primers, while poor primers give incomplete fragments, non-specific amplification or no amplification. There is, a priori, no known method of prediction the usefulness of a primer pair in the NASBA™ system. Knowledge of the chemical composition and structure of primers is not sufficient to allow prediction of their usefulness in an amplification system, including NASBA™.

In a preferred embodiment, two DNA primers of the following description are used in the NASBA™ process. A P1 primer consisting of four regions, going from the 5' to the 3' end: an overhang sequence; a sequence that is a T7 RNA polymerase promoter; a spacer region where transcription initiates; and a region that is complementary to the RNA template and hybridizes directly to it. A P2 primer, which consists of a single region that hybridizes to the complementary strand of the RNA sequence to be amplified. The P1 primer initially hybridizes to the RNA template and serves as a primer for reverse transcriptase to initiate first strand cDNA synthesis. After second strand synthesis, the completed cDNA contains the T7 RNA polymerase promoter site from the P1 primer. T7 RNA polymerase can now bind and initiate RNA synthesis, which is the amplification phase of the NASBA™ reaction.

The present invention is directed to primer combinations, P1 and P2, that are useful for the amplification of a mycobacterial 16S rRNA sequence by NASBA™. Table 1 lists the various P1 and P2 primers that were designed and tested. Primers are not evaluated individually but in pairs; thus, it is a primer pair that is useful for NASBA™.

737A; 727B/737B; 201/101; 202/102; 201B/102B. Two additional P1 primers were designed and tested that are from conserved regions and were believed to have minimal secondary structure, but were not elucidated using the OLIGO program: 50.1 and 299.

Since most primer pairs, as originally designed, did not work well, all random combinations of primers were examined. Among all combinations of P1 and P2 primers tested, the pair 201/50.1 was judged to be the best for amplification of the mycobacterial template based on the following observations. Primarily one band of the correct size (about 242 bases) was observed on urea-polyacrylamide gels, whereas most primer pairs gave multiple bands, smaller than full length, on urea-polyacrylamide and/or agarose gels. Sensitivity and detection of template, as measured by a positive

TABLE 1

PRIMER SEQUENCES

P1 Primers 50.1    AGT AAT T[TA ATA CGA CTC ACT ATA] GGG (AGT CTG GGC CGT ATC TCA GTC CC)
     [SEQ ID NO: 1]
737A    AGT AAT T[TA ATA CGA CTC ACT ATA] GGG (AGT GTG GCC GGA CAC CCT CTC A)
     [SEQ ID NO: 2]
101    AAT T[TA ATA CGA CTC ACT ATA] (GTT CGT CGA TGG TGA AAG AGG)
     [SEQ ID NO: 3]
102    AAT T[TA ATA CGA CTC ACT ATA] (GAG TCT GGG CCG TAT CTC A)
     [SEQ ID NO: 4]
102B    AAT T[TA ATA CGA CTC ACT ATA] GGG (AGG AGT CTG GGC CGT ATC TCA)
     [SEQ ID NO: 5]
299    AAT T[TA ATA CGA CTC ACT ATA] GGG (AGA ACT GCT GCC TCC CGT AGG A)
     [SEQ ID NO: 6]

P2 Primers

727A    (AAC ACG TGG GTA ATC TGC CCT GCA)
     [SEQ ID NO: 7]
727B    (TGA GTA ACA CGT GGG TGA TCT GCC)
     [SEQ ID NO: 8]
201    (TGG CGA ACG GGT GAG TAA CA)
     [SEQ ID NO: 9]
201B    (GAG TGG CGA ACG GGT GAG TA)
     [SEQ ID NC: 1O]
202    (TGG GAA ACT GGG TCT AAT)
     [SEQ ID NO: 11]

Oligonucleotides were synthesized on a Milligen/Biosearch Cyclone Plus DNA Synthesizer. After elution from the synthesizer column and overnight deprotection at room temperature, the oligonucleotides were purified by reverse phase chromatography using an OPEC column (Clontach, San Diego (CA). The primers were further purified by denaturing gel electrophoresis using a BioRad Model 491 Prep Cell.
P1 primers contain the T7 RNA polymerase promotor region, denoted by [ ] and the hybridization region, denoted by ( ). P2 primers contain only the hybridization region.

All combinations of P1 and P2 primers were evaluated in NASBA™ using purified 16S ribosomal RNA isolated from *Mycobacteria bovis* BCG as template. Primers were designed and chosen for evaluation based on a number of considerations. First, the published nucleic acid sequences for mycobacterial 16S rRNA in the GenBank and EMBL data bases were obtained and a region that is conserved in the majority of mycobacterial species was determined. Second, the T7 RNA polymerase promoter sequence is known (*Journal of Molecular Biology* 166:477–535, 1983) as well as some information regarding its use in NASBA™ primers (PCR Methods and Applications, 1:25–33, 1989). Third, focusing on the aforementioned conserved region, the OLIGO primer analysis software program (National Biosciences, 3650 Annapolis Lane, Plymouth, Minn. 55447) was used in an effort to predict useful pairs and eliminate primer choices containing hairpins and loops, primers capable of self hybridization and primer pairs capable of hybridizing to one another. The following primer pairs were designed using the above considerations: 727/737; 727A/

ELGA (enzyme linked gel assay disclosed in van der Vliet et al, *Journal of General Microbiology,* supra) or ECL assay, was as low as 10 copies of template, better than for any other primer pair tested, most by several orders of magnitude. Table 2 shows the comparison of primer pair efficiency in the NASBA™ system according to the present invention.

TABLE 2

COMPARISON OF PRIMER PAIR EFFICIENCY
IN AMPLIFYING *M. BOVIS* BCG 16S RIBOSOMAL RNA

| Primer Pair | ELGA Assay | ECL Assay |
|---|---|---|
| 201/50.1 | $10^1$ | $10^1$ |
| 727B/50.1 | $10^3$ | $10^1$ |
| 202/50.1 | $10^3$ | $10^3$ |
| 202/102 | $10^5$ | $10^5$ |
| 201/737B | $10^6$ | $10^5$ |
| 201/299 | ND | $10^5$ |

TABLE 2-continued

COMPARISON OF PRIMER PAIR EFFICIENCY
IN AMPLIFYING M. BOVIS BCG 16S RIBOSOMAL RNA

| Primer Pair | ELGA Assay | ECL Assay |
|---|---|---|
| 201/101 | $10^7$ | $10^6$ |
| 727B/737B | $10^7$ | $10^6$ |
| 202/737B | $10^7$ | $10^7$ |
| 201/102 | $10^8$ | $10^7$ |
| 727/102 | $10^8$ | $10^8$ |
| 202/101 | NA | NA |
| 201/102B | NA | NA |
| 201B/50.1 | NA | NA |
| 202/299 | ND | NA |
| 737B/299 | ND | NA |

NA = no amplification
ND = not done

Primers 201 and 50.1 are from regions of the ribosomal RNA gene that are highly conserved between mycobacterial species. Therefore, this pair allows the amplification of all pathogenic Mycobacteria. Primer selection is critical for amplification of the 16S ribosomal RNA template by NASBA™. For example, 201 and 201B are identical except for a three base shift. When 201B is paired with 50.1, there is no detectable amplification of template, while 10 copies of template can be detected by amplification with 201 and 50.1. Primers 50.1 and 102 are also from the same region, yet the sensitivity with 201 and 102 as a primer pair is about 6 orders of magnitude poorer than with 201 and 50.1.

Once the 16S ribosomal RNA is amplified using the P1 and P2 primers set forth above, detection of the amplificate can be done using the following preferred probes, which can be labeled with an appropriate label, such as biotin, Tris(2, 2'-bipyridine) ruthenium (II)—an electrochemiluminescent reporter group—or horseradish peroxidase (HRP):

*M. tuberculosis* genome which is unique to this series. It is, therefore, useful as a species-specific probe in the diagnostic method. OT998A is derived form a unique genomic sequence of *M. avium,* and so is useful as a species specific probe for detection in a sample of *M. avium.* Finally, OT997 is a sequence derived from *M. intracellulare* that is unique to this species and so can be used to detect this species. Detection methods using capture and detection (labelled) probes are known in the art. The aforementioned probes can be used as "detection" (i.e., labelled) probes or "capture" probes. For instance, OT728 can be biotinylated and attached to a streptavidin substrate and act as the capture probe, and any or all of the OT999A, OT998A and OT997 can be labelled with an appropriate detection label (e.g., HRP or ECL label) and be used to detect the specific species. It can also work the other way around: OT728 can be the detection (labeled) probe, and any or all of the other probes can be biotinylated and act as capture probes.

The present invention is not limited to the above-noted probes, which are only presented as examples. Other mycobacterial 16S rRNA probes are known and, to the extent that they can bind to the amplified RNA, are included as useful in the present invention. Such probes are disclosed in B öddinghaus et al., *Journal of Clinical Microbiology,* 28:1751–1759 (1990) and EP 0 528 306 A2 (1993), both of which are incorporated herein by reference.

The present invention further relates to a method of detecting Mycobacteria in a sample using the above-disclosed primers and probes, and to test kits to be used in such a diagnostic test. A test kit according to the present invention may comprise a set of primers according to the invention and, optionally, one or more probes according to the invention. Such a test kit may additionally comprise suitable amplification reagents such as DNA and/or RNA polymerases and mononucleotides.

The Examples given below are presented only for illustrative purposes and do not limit the scope of the present invention.

TABLE 3

PROBES

| NAME | SEQUENCE | LENGTH |
|---|---|---|
| OT 728 | 5'-GATAAGCCTGGGAAACTGGGTCTAATA-3' [SEQ ID NO: 12] | 27 |
| OT999A (MTB) | 5'-ACGGGATGCATGTCTTG-3' [SEQ ID NO: 13] | 18 |
| OT998A (Avium) | 5'-TCAAGACGCATGTCTTCT-3' [SEQ ID NO: 14] | 18 |
| OT997 (Intrac.) | 5'-TTTAGGCGCATGTCTTTA-3' [SEQ ID NO: 15] | 18 |

Oligonucleotides containing 3'-amine or 3'biotin groups were prepared on a Milligen/Biosearch Cyclone Plus DNA synthesizer using either 3'-amine on CPG or 3'-biotin on CPG, respectively, from Glenn Research (Sterling, Va.). These oligos were purified by reverse phase chromatography on $C_{18}$, lyophilized, and resuspended in $H_2O$. Coupling of HRP label to purified $NH_2$-oligos was done according to R. I. Amann et al., *Applied and Environmental Microbiology,* 58:3007–3011 (1992). ECL probes were prepared by coupling Tris(2,2')-bipyridine ruthenium (II) (Igen Inc, Rockville, Md.) to purified $NH_2$-oligos following protocols supplied by Igen.

The probe OT728 is derived from a region substantially conserved in the majority of Mycobacteria species, and allows for the detection of any Mycobacteria present in a sample. The probe OT999A is derived from a region of the

EXAMPLE 1

Comparison of Primer Pair Efficiency in Amplifying *M. bovis* BCG 16S Ribosomal RNA Ribosomal RNA was extracted and purified from *M. bovis* BCG in accordance with the method of Crestfield et al., *Journal of Biological Chemistry* 216:185–193, 1955. Dilutions of RNA (from $10^{10}$ to $10^1$ copies per 5 $\mu$l) were prepared in water.

Amplification by NASBA™ was performed as follows: for each primer pair a 5 $\mu$l aliquot of RNA sample was transferred to 18 $\mu$l of amplification mastermix (which includes the respective primer pairs listed in Table 2). Reaction tubes were incubated at 65° C. for 5 minutes followed by 41° C. for 5 minutes. Then, 2 $\mu$l of enzyme solution (8 units AMV reverse transcriptase, 0.1 units RNase H, and 40 units T7 RNA polymerase) was added and the reaction was held at 41° C. for 90 minutes. The amplification was terminated by freezing the tubes at −20° C. until detection was preformed. The reaction contained 40 mM Tris/HCl, pH 8.5, 12 mM MgCl$_2$, 5 mM DTT, 1 mM of each dNTP, 2 mM ATP, CTP and UTP, 1.5 mM GTP, 0.5 mM ITP, 15% v/v DMSO and 0.2 µM each primer. Concentration of KCl in the reaction varied between 80 mM and 120 mM, depending on primer set.

ELGA (enzyme linked gel assay) detection was performed as disclosed in Van Der Vliet et al., *Journal of General Microbiology* 139:2423–2429, 1993. Briefly, 2 µl of amplified RNA and 2 µl of horseradish peroxidase labeled 999 A probe ($10^{10}$ molecules) were mixed in 1×SSC at 41° C. for 15 minutes. Two µl of the hybridized sample was then loaded on a 7% polyacrylamide gel containing 0.04% (w/v) dextran sulphate and run in TBE buffer until the marker dye xylene cyanol just ran off the gel. The hybrid and free probe were visualized by placing the gel in 12 ml of a TMB-urea peroxidase substrate solution. After 10 minutes of gentle shaking in substrate solution at ambient temperature the blue bands were visible.

Electrochemiluminescent (ECL) detection of amplified RNA was performed using a NASBA™ QR system (Organon Teknika Corp., Durham, N.C.). Streptavidin-coated magnetic beads (Dynal, Lake Success, N.Y.) were prepared with a biotin labeled capture probe (OT728) for Mycobacteria. Ten µl of capture beads were added to 10 µl of a species-specific detection probe (999 A) in 6.25×SSC and 5 µl amplified RNA. Hybridization proceeded for 30 minutes at 41° C. Assay buffer (300 µl) was then added and electrochemiluminescence was measured on the instrument.

Figure 1:
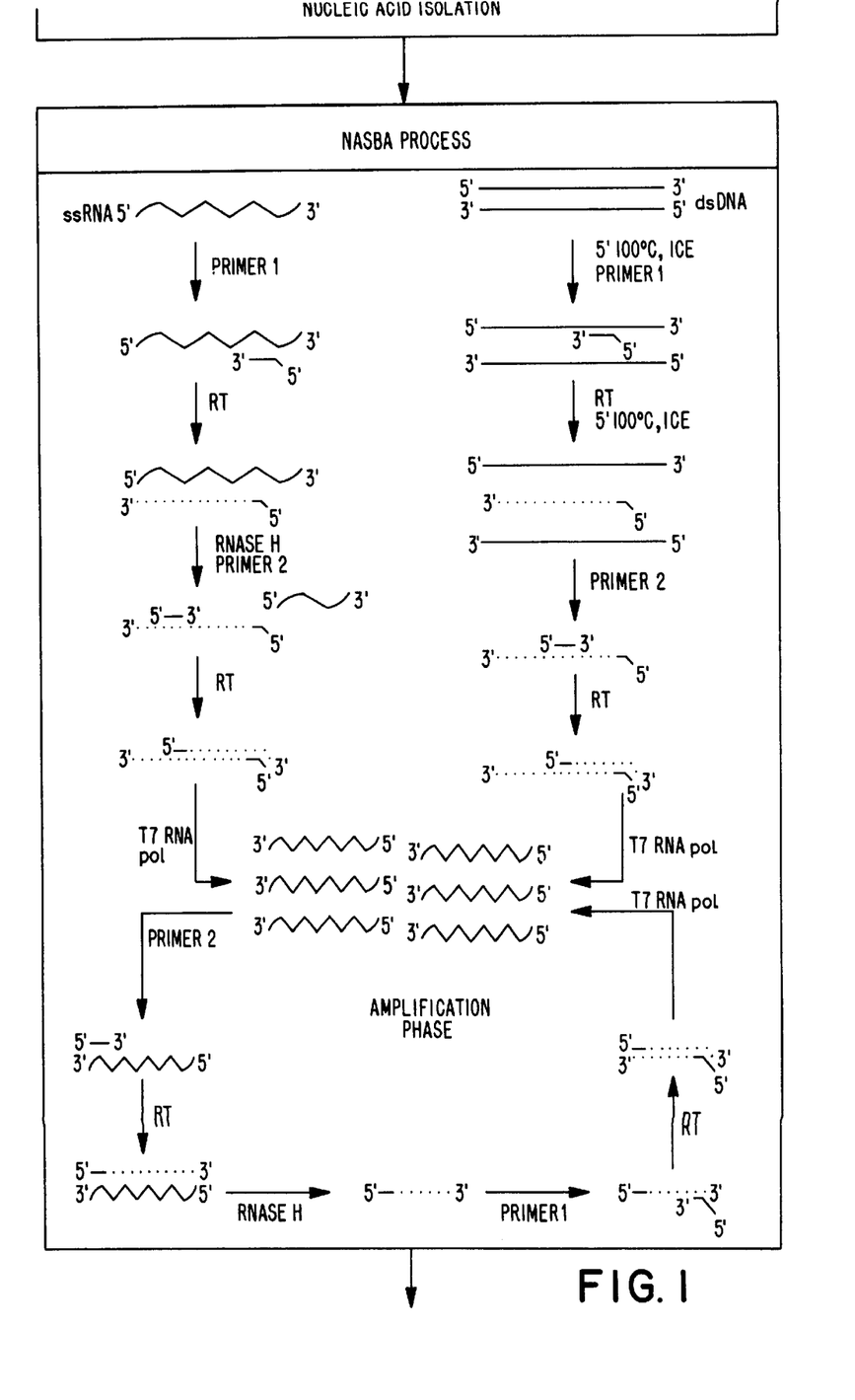
Figure 2A:
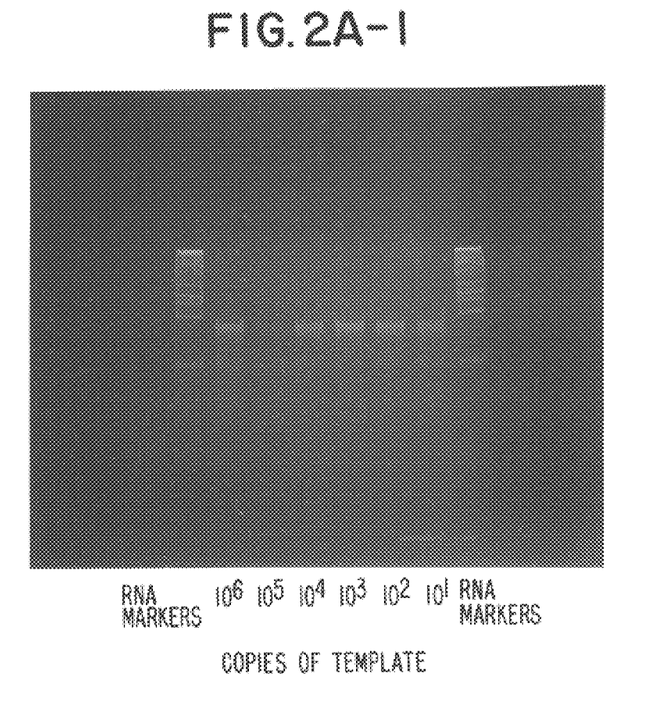
Figure 2A:
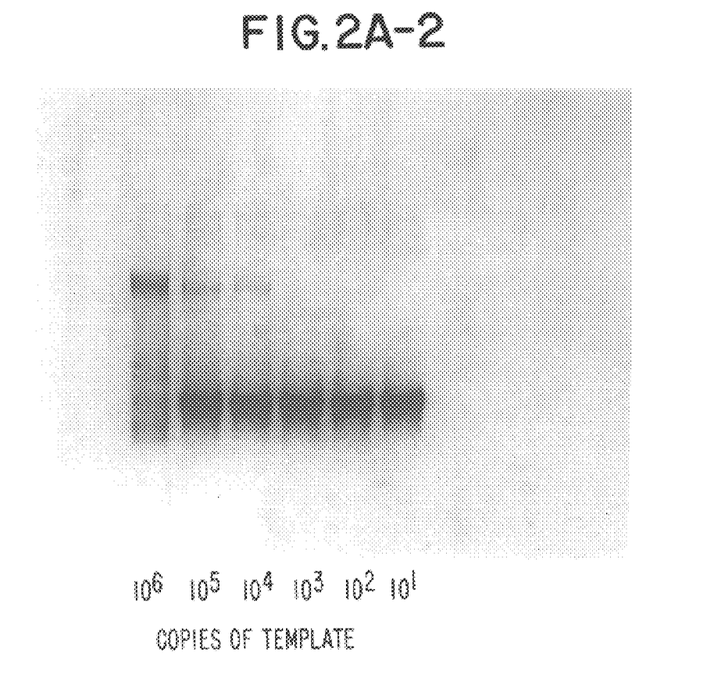
Figure 2B:
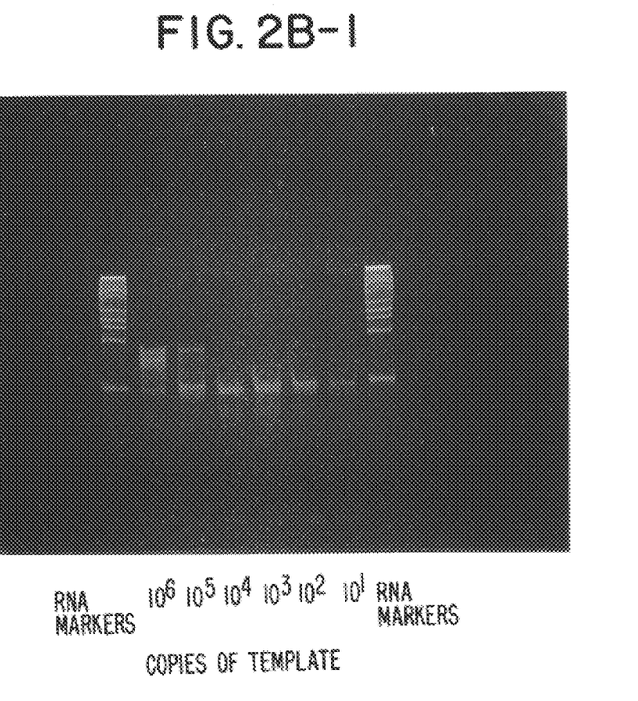
Figure 2B:
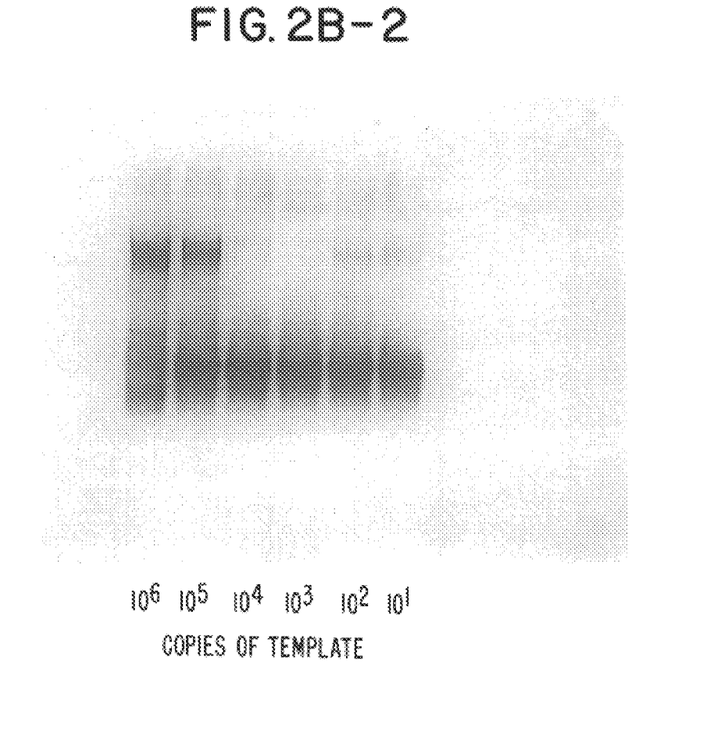
Figure 2C:
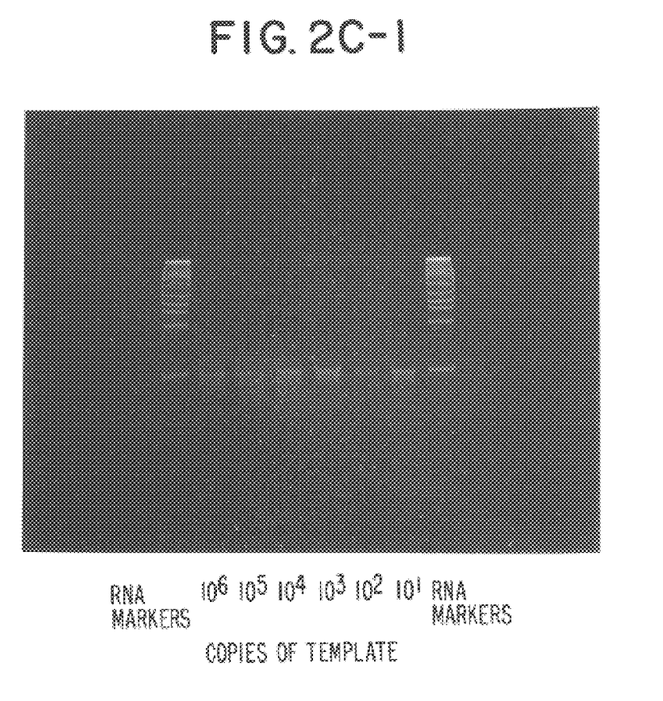
Figure 2C:
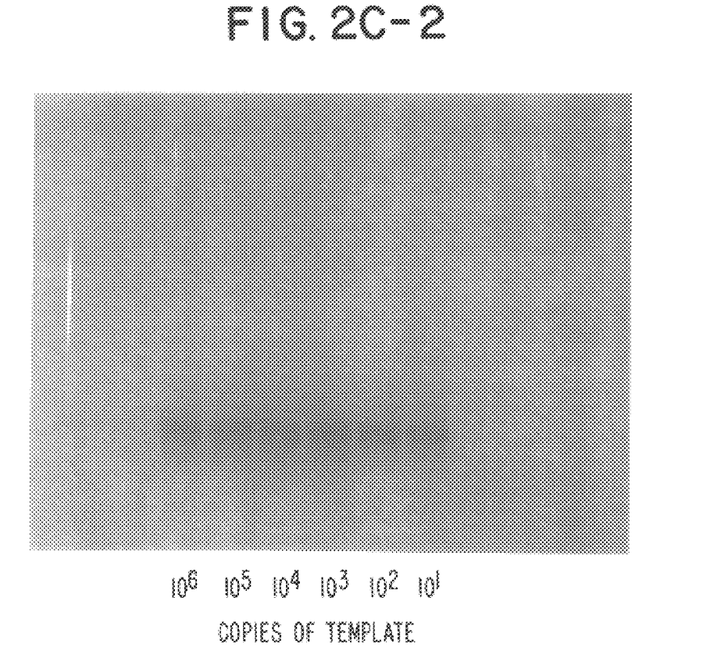

The results are given in Table 2, above, and in FIG. 2. In addition, it was also determined that, for the primer pair 201/50.1, the optimum level of potassium chloride is about 120 mM, although levels of 80–130 mM potassium chloride were useful.

We claim:

1. An oligonucleotide primer for amplifying the 16S ribosomal RNA of a mycobacterial species, wherein said primer contains a sequence consisting of the sequence: 5'-AGT CTG GGC CGT ATC TCA GTC CC-3'[SEQ ID NO: 16], wherein said sequence is complementary to a region of the 16S ribosomal RNA of a mycobacterial species.

2. A pair of oligonucleotide primers for amplifying a region of the 16S ribosomal RNA of a mycobacterial species, wherein the first primer contains a sequence consisting of: 5'-AGT CTG GGC CGT ATC TCA GTC CC-3' [SEQ ID NO: 16] and the second primer contains a sequence consisting of: 5'-TGG CGA ACG GGT GAG TAA CA-3' [SEQ ID NO: 9].

3. The oligonucleotide primer of claim 1, which further contains a polymerase promoter nucleic acid sequence.

4. The oligonucleotide primer of claim 3, which consists of the nucleic acid sequence: 5'-AGT AAT TTA ATA CGA CTC ACT ATA GGG AGT CTG GGC CGT ATC TCA GTC CC-3'[SEQ ID NO: 1].

5. The pair of oligonucleotide primers of claim 2, wherein the first primer further contains a polymerase promoter nucleotide sequence.

6. The pair of oligonucleotide primers according to claim 5, wherein the first primer has the sequence: 5'-AGT AAT TTA ATA CGA CTC ACT ATA GGG AGT CTG GGC CGT ATC TCA GTC CC-3'[SEQ ID NO: 1].

7. A process for amplifying a target ribonucleic acid in the 16S ribosomal RNA of a mycobacterial species, comprising the steps of:

(a) hybridizing to single-stranded ribosomal RNA a primer containing a polymerase promoter nucleic acid sequence and the sequence: 5'-AGT CTG GGC CGT ATC TCA GTC CC-3'[SEQ ID NO: 16];

(b) using reverse transcriptase to extend said first primer to thereby obtain an RNA-DNA hybrid, and then separating the DNA strand therefrom;

(c) hybridizing to said single-stranded DNA a second primer consisting of the nucleic acid sequence: 5'-TGG CGA ACG GGT GAG TAA CA-3'[SEQ ID NO: 9] and extending said second primer to thereby obtain a double-stranded DNA template containing a functional polymerase promoter; and (d) adding RNA polymerase to said double-stranded DNA of step (c) to thereby generate multiple copies of single-stranded RNA.

8. The method of claim 7, wherein the single-stranded RNA obtained in step (d) acts as a template for the synthesis of double-stranded DNA by steps (a) through (c), thereby establishing a cyclic phase of amplification.

9. The method of claim 7, wherein in step (b) RNase H is used to create single-stranded DNA from the RNA-DNA hybrid.

10. The method of claim 7, wherein the first primer has a nucleic acid sequence consisting of: 5'-AGT AAT TTA ATA CGA CTC ACT ATA GGG AGT CTG GGC CGT ATC TCA GTC CC-3'[SEQ ID NO: 1].

11. A method for the detection of Mycobacteria in a sample, comprising the steps of:

(a) hybridizing to the single-stranded ribosomal RNA a primer containing a polymerase promoter nucleic acid sequence and the sequence: 5'-AGT CTG GGC CGT ATC TCA GTC CC-3'[SEQ ID NO: 16];

(b) using reverse transcriptase to extend said first primer to thereby obtain a single-stranded DNA;

(c) hybridizing to said single-stranded DNA a second primer having the nucleic acid sequence: 5'-TGG CGA ACG GGT GAG TAA CA-3'[SEQ ID NO: 9] and extending said second primer to thereby obtain a double-stranded DNA template containing a functional polymerase promoter;

(d) adding RNA polymerase to said double-stranded DNA of step (c) to thereby generate multiple copies of single-stranded RNA;

(e) mixing the RNA so amplified with a sequence specific oligonucleotide probe selected from the group consisting of SEQ ID NOs: 12, 13, 14 and 15; and (f) detecting hybrids formed between said nucleic acid and said probe.

12. A kit for detecting and optionally identifying a mycobacterial species in a sample, wherein the kit comprises a pair of primers, wherein a first primer comprises an RNA polymerase promoter and a hybridizing sequence having the sequence: 5'-ATG CTG GGC CGT ATC TCA GTC CC-3' [SEQ ID NO: 16], and the second primer has the sequence: 5'-TGG CGA ACG GGT GAG TAA CA-3'[SEQ ID NO: 9].

13. The kit of claim 12, further comprising an oligonucleotide probe containing a nucleic acid sequence capable of hybridizing to the region of the 16S ribosomal RNA amplified by the first primer and the second primer.

* * * * *

```
                       SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthesized DNA primer"

(iii) HYPOTHETICAL: NO (iv) ANTI-SENSE: NO (ix) FEATURE:
          (A) NAME/KEY: misc_feature
          (B) LOCATION: 8..24
          (D) OTHER INFORMATION: /note= "T7 RNA polymerase promoter"

(ix) FEATURE:
          (A) NAME/KEY: misc_feature
          (B) LOCATION: 28..50
          (D) OTHER INFORMATION: /note= "hybridization region"

(xi) SEQUENCE DESCRIPTION: SEQ ID NO:1:

AGTAATTTAA TACGACTCAC TATAGGGAGT CTGGGCCGTA TCTCAGTCCC                 50

(2) INFORMATION FOR SEQ ID NO:2:

(i) SEQUENCE CHARACTERISTICS:
          (A) LENGTH: 49 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "synthetic DNA primer"

(iii) HYPOTHETICAL: NO (iv) ANTI-SENSE: NO (ix) FEATURE:
          (A) NAME/KEY: misc_feature
```

(B) LOCATION: 8..24
        (D) OTHER INFORMATION: /note= "T7 RNA polymerase promoter"

(ix) FEATURE:
        (A) NAME/KEY: misc_feature
        (B) LOCATION: 28..49
        (D) OTHER INFORMATION: /note= "hybridization region"

(xi) SEQUENCE DESCRIPTION: SEQ ID NO:2:

AGTAATTTAA TACGACTCAC TATAGGGAGT GTGGCCGGAC ACCCTCTCA                49

(2) INFORMATION FOR SEQ ID NO:3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(iii) HYPOTHETICAL: NO (iv) ANTI-SENSE: NO (ix) FEATURE:
        (A) NAME/KEY: misc_feature
        (B) LOCATION: 5..21
        (D) OTHER INFORMATION: /note= "T7 RNA polymerase promoter"

(ix) FEATURE:
        (A) NAME/KEY: misc_feature
        (B) LOCATION: 22..42
        (D) OTHER INFORMATION: /note= "hybridization region"

(xi) SEQUENCE DESCRIPTION: SEQ ID NO:3:

AATTTAATAC GACTCACTAT AGTTCGTCGA TGGTGAAAGA GG                       42

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(iii) HYPOTHETICAL: NO (iv) ANTI-SENSE: NO (vi) ORIGINAL SOURCE:
        (A) ORGANISM: Mycobacterium bovis (ix) FEATURE:
        (A) NAME/KEY: misc_feature
        (B) LOCATION: 5..21
        (D) OTHER INFORMATION: /note= "T7 RNA polymerase promoter"

(ix) FEATURE:
        (A) NAME/KEY: misc_feature
        (B) LOCATION: 22..40
        (D) OTHER INFORMATION: /note= "hybridization region"

(xi) SEQUENCE DESCRIPTION: SEQ ID NO:4:

AATTTAATAC GACTCACTAT AGAGTCTGGG CCGTATCTCA                          40

(2) INFORMATION FOR SEQ ID NO:5:

(i) SEQUENCE CHARACTERISTICS:
        (A) LENGTH: 45 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(iii) HYPOTHETICAL: NO (iv) ANTI-SENSE: NO (ix) FEATURE:
        (A) NAME/KEY: misc_feature
        (B) LOCATION: 5..21
        (D) OTHER INFORMATION: /note= "T7 RNA polymerase promoter"

(ix) FEATURE:
        (A) NAME/KEY: misc_feature
        (B) LOCATION: 25..45
        (D) OTHER INFORMATION: /note= "hybridization region"

(xi) SEQUENCE DESCRIPTION: SEQ ID NO:5:

AATTTAATAC GACTCACTAT AGGGAGGAGT CTGGGCCGTA TCTCA                    45

(2) INFORMATION FOR SEQ ID NO:6:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(iii) HYPOTHETICAL: NO (iv) ANTI-SENSE: NO (ix) FEATURE:
        (A) NAME/KEY: misc_feature
        (B) LOCATION: 5..21
        (D) OTHER INFORMATION: /note= "T7 RNA polymerase promoter"

(ix) FEATURE:
        (A) NAME/KEY: misc_feature
        (B) LOCATION: 25..46
        (D) OTHER INFORMATION: /note= "hybridization region"

(xi) SEQUENCE DESCRIPTION: SEQ ID NO:6:

AATTTAATAC GACTCACTAT AGGGAGAACT GCTGCCTCCC GTAGGA                   46

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(iii) HYPOTHETICAL: NO (iv) ANTI-SENSE: NO (xi) SEQUENCE DESCRIPTION: SEQ ID NO:7:

AACACGTGGG TAATCTGCCC TGCA                                           24

(2) INFORMATION FOR SEQ ID NO:8:

(i) SEQUENCE CHARACTERISTICS:
        (A) LENGTH: 24 base pairs (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA primer"

(iii) HYPOTHETICAL: NO (iv) ANTI-SENSE: NO (xi) SEQUENCE DESCRIPTION: SEQ ID NO:8:

TGAGTAACAC GTGGGTGATC TGCC                                                     24

(2) INFORMATION FOR SEQ ID NO:9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA primer"

(iii) HYPOTHETICAL: NO (iv) ANTI-SENSE: NO (xi) SEQUENCE DESCRIPTION: SEQ ID NO:9:

TGGCGAACGG GTGAGTAACA                                                          20

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA primer"

(iii) HYPOTHETICAL: NO (iv) ANTI-SENSE: NO (xi) SEQUENCE DESCRIPTION: SEQ ID NO:10:

GAGTGGCGAA CGGGTGAGTA                                                          20

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA primer"

(iii) HYPOTHETICAL: NO (iv) ANTI-SENSE: NO (xi) SEQUENCE DESCRIPTION: SEQ ID NO:11:

TGGGAAACTG GGTCTAAT                                                            18

(2) INFORMATION FOR SEQ ID NO:12:

(i) SEQUENCE CHARACTERISTICS:
            (A) LENGTH: 27 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA probe"

(iii) HYPOTHETICAL: NO (iv) ANTI-SENSE: YES (xi) SEQUENCE DESCRIPTION: SEQ ID NO:12:

GATAAGCCTG GGAAACTGGG TCTAATA                                                27

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA probe to
            detect M. tuberculosis"

(iii) HYPOTHETICAL: NO (iv) ANTI-SENSE: YES (xi) SEQUENCE DESCRIPTION: SEQ ID NO:13:

ACGGGATGCA TGTCTTG                                                           17

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA probe to
            detect M. avium"

(iii) HYPOTHETICAL: NO (iv) ANTI-SENSE: YES (xi) SEQUENCE DESCRIPTION: SEQ ID NO:14:

TCAAGACGCA TGTCTTCT                                                          18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA probe for
            detecting M. intracellulare"

(iii) HYPOTHETICAL: NO (iv) ANTI-SENSE: YES (xi) SEQUENCE DESCRIPTION: SEQ ID NO:15:

TTTAGGCGCA TGTCTTTA                                                          18

(2) INFORMATION FOR SEQ ID NO:16:
```

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA hybrization sequence"

(iii) HYPOTHETICAL: NO (iv) ANTI-SENSE: YES (xi) SEQUENCE DESCRIPTION: SEQ ID NO:16:

AGTCTGGGCC GTATCTCAGT CCC                                                23